United States Patent [19]

Valenty

[11] Patent Number: 4,524,009

[45] Date of Patent: Jun. 18, 1985

[54] DETERGENT BUILDER

[75] Inventor: Vivian B. Valenty, Schenectady, N.Y.

[73] Assignee: A. E. Staley Manufacturing Company, Decatur, Ill.

[21] Appl. No.: 575,421

[22] Filed: Jan. 31, 1984

[51] Int. Cl.$^3$ ............................................. C11D 00/00
[52] U.S. Cl. ................................... 252/89.1; 252/82; 252/180; 252/DIG. 11; 562/583
[58] Field of Search .................. 562/583; 252/180, 82, 252/DIG. 11, 89.1

[56] References Cited

U.S. PATENT DOCUMENTS

| | | | |
|---|---|---|---|
| 3,128,287 | 4/1964 | Berg et al. | 549/252 |
| 3,692,685 | 9/1972 | Lamberti et al. | 252/174.14 |
| 3,954,858 | 5/1976 | Lamberti et al. | 526/583 |
| 4,002,676 | 1/1977 | Borggrefe | 252/110 |
| 4,017,541 | 4/1977 | Stubbs et al. | 252/132 |
| 4,021,376 | 5/1977 | Lamberti et al. | 252/542 |
| 4,025,450 | 5/1977 | Lamberti et al. | 526/583 |
| 4,219,672 | 8/1980 | Borggrefe | 562/583 |

FOREIGN PATENT DOCUMENTS

| | | |
|---|---|---|
| 2147780 | 3/1973 | Fed. Rep. of Germany . |
| 2408591 | 9/1975 | Fed. Rep. of Germany . |

OTHER PUBLICATIONS

Journal Amer. Oil Chemists' Soc., 55 pp. 58–65 (1978) Crutchfield.

"Nitrogen–and Phosphorous–Free Strong Sequestering Blds.", Kemper, et al., Tenside Detergents, 12 pp. 47–51 (1975).

Org. Builder Salts as Replacements for Sodium Tripolyphosphate (I) Tenside Detergents, 10 pp. 119–125, Matzner, et al. (1973).

Org. Builder Salts as Replacements for Sodium Tripolyphosphate (II), Tenside Detergents, 10 pp. 239–245, Matzner et al. (1973).

*Primary Examiner*—Paul Lieberman
*Assistant Examiner*—Hoa Van Le
*Attorney, Agent, or Firm*—Forrest L. Collins; James B. Guffey

[57] ABSTRACT

The present invention describes compounds of the formula:

A. $MOOCCH_2(MOOC)HCOCH_2CH(OH)CH_2OCH(COOM)CH_2COOM$

B. $HOCH_2HC(OH)CH_2OCH(COOM)CH_2COOM$

C. $HOCH_2CH[OCH(COOM)CH_2COOM]CH_2OCH(COOM)CH_2COOM$ and

D. And mixtures thereof where M is a salt-forming cation or hydrogen or mixtures thereof.

This invention also discloses products prepared by the process of reacting glycerine and a source of maleic acid in the presence of an alkaline earth metal hydroxide.

20 Claims, No Drawings

DETERGENT BUILDER

BACKGROUND OF THE INVENTION

1. Field of the Invention

This invention describes detergent builder materials which are suitable as partial or total replacements for phosphates or nitrogen-containing builders.

2. Description of the Art Practices

Detergent builders are used to enhance the activity of the detergent or surfactant material used for cleaning. A detergent product typically contains a surface-active material (surfactant) which is used to lift dirt from the fabrics and to penetrate into the fabrics to remove embedded soil. Typically, these surface-active agents are the sodium salts of anionic materials. As the bulk of heavy-duty detergents are of the anionic nature, there exists an interference in the cleaning mechanism when calcium or magnesium ions (which are present as water hardness or body soil) react with the anion. In the case of body soil, the surfactant will become fixed onto the fabric due to the formation of the insoluble calcium or magnesium salt. The calcium or magnesium cations within the water cause the surfactant to be inactivated due to the formation of insoluble salts.

Heavy-duty liquid detergent products have been formulated but not successfully utilizing a detergent builder. This is most evident as the common detergent builders employed tend to be phosphate salts which would precipitate out of a liquid composition when utilized at an effective amount for cleaning. Although heavy-duty liquid detergent products are often formulated with a substantial amount of a nonionic surfactant such as ethoxylated alcohol, the ability of calcium and magnesium ions to fix on the soil lead to the desirable inclusion of a detergent builder.

As mentioned previously, phosphates salts such as sodium tripolyphosphate or sodium pyrophosphate have been extensively used. Several states have outlawed the use of phosphorous-containing compounds in detergent products due to the eutrification enhancement caused by the presence of the phosphates. Replacements for phosphates as builders in detergent products have included organic nitrogen-containing compounds, carbonates and aluminosilicates. Each of these materials has its own particular negatives associated therewith. For instance, concern has been expressed over the widespread usage of organic nitrogen-containing compounds due to potential carcinogenic effects in the water supply. Carbonates have been widely employed but are generally ineffective as detergent builders as they result in the build-up of scale due to the insoluble calcium carbonate formation. Aluminosilicates are insoluble materials commonly used in water softeners. The aluminosilicates are disadvantageous in that, as an insoluble material, they can foul sewer lines and water-treatment facilities if used in excessive amounts. The aluminosilicates are also not useful in liquid products due to their insolubility.

It is, therefore, desirable to formulate detergent products containing builders which do not contain nitrogen or phosphorous and which are water-soluble and are biodegradable. It has been reported in an article entitled "Nitrogen-and Phosphorous-Free Strong Sequestering Building", Kemper et al, *Tenside Detergents*, 12 page 47–51 (1975) that the reaction product of ethylene glycol and dimethyl diazomalonate results in such a compound. While this material avoids the presence of phosphorous or nitrogen in the desired compound, it does allow for the potential presence of the diazo compound in the environment and requires exaggerated temperature and the use of copper as a catalyst to form the desired compound. The efficacy of this compound as reported by the authors is rated at about 97% of sodium tripolyphosphate. Other compounds disclosed in the Kemper reference show Builder M (2-oxa-1,1,3-propanetricarboxylic acid) at 93% of sodium tripolyphosphate. A further proposed material 2-oxa-1,3,4-butanetricarboxylic acid (CMOS) is rated at only 90% of sodium tripolyphosphate.

It is further recommended by the author that the reader review U.S. Pat. 3,692,685, issued to Lamberti et al on Sept. 19, 1972, as well as U.S. Pat. No. 3,128,287, issued to Berg on Apr. 7, 1964. Further disclosures of carboxylic acid materials are found in U.S. Pat. 4,021,376 issued to Lamberti et al on May 3, 1977.

German Pat. No. 2,147,780, published on Mar. 29, 1973, to Kandler et al and German Pat. No. 2,408,591, published on Sept. 4, 1975, to Borggrefe et al, also concern the general subject matter of the present invention. The article of Crutchfield entitled "Organic Builders: A Review of Worldwide Efforts to Find Organic Replacements for Detergent Phosphates" published in the *JAOCS* of 55, pages 58–65 (1978), and the Matzener et al article entitled "Organic Builder Salts as Replacements for Sodium Tripolyphosphate (I)" in *Tenside Detergents*, 10, pages 119–125 and 239–245 (1973) also provide useful information concerning the general scope of the present invention.

To the extent that each of the foregoing references are pertinent to this disclosure, they are herein incorporated by reference.

The present invention deals with the formation of a detergent builder from readily available materials which do not contain phosphorous or nitrogen. The new builder is readily biodegradable, is readily soluble in water and has superior detergent builder capabilities than previously known related compounds.

Throughout the specification and claims, percentages and ratios are by weight, pressures are in atmospheres and temperatures are in degrees Celsius unless otherwise indicated.

SUMMARY OF THE INVENTION

This invention describes a compound of the formula: $MOOCCH_2(MOOC)HCOCH_2CH(OH)CH_2OCH(COOM)CH_2COOM$ wherein M is a salt-forming cation or hydrogen or mixtures thereof.

Further described is a compound of the formula: $HOCH_2HC(OH)CH_2OCH(COOM)CH_2COOM$ wherein M is a salt-forming cation or hydrogen or mixtures thereof.

A further material obtained is a compound of the formula: $HOCH_2CH[OCH(COOM)CH_2COOM]CH_2OCH(COOM)CH_2COOM$ wherein M is a salt-forming cation or hydrogen or mixtures thereof.

Mixtures of the foregoing are included herein as well as the product obtained from the process of reacting glycerine and a source of maleic acid in the presence of an alkaline earth hydroxide.

The following invention also describes a method of cleaning fabrics through the use of the foregoing compounds to control calcium, magnesium and iron ions during the cleaning process.

DETAILED DESCRIPTION OF THE INVENTION

The backbone of the claimed components of the present invention is glycerine. Glycerine is a trihydroxylic compound containing two primary hydroxyl groups and one centrally located secondary hydroxyl group. The positioning of the secondary hydroxyl group makes it less likely to react to give the desired compounds of the present invention. The primary compound obtained herein is the 1,3 disubstituted product. The secondary materials obtained herein are the 1,2 disubstituted materials and the 1 (being equivalent with the 3 position) substituted mono adduct. Glycerine is a readily available material and any source may be utilized to obtain the compounds described herein.

The second reactant material in the present invention is preferably maleic anhydride. Maleic acid may also be used, however, maleic anhydride is less expensive and readily available. If it is desired to conduct the reaction through maleic acid, the maleic anhydride may be simply converted through the addition of water to give the corresponding acid. The term maleic acid source is defined to mean a material which will generate maleic acid which is useable to give the products of the present invention.

An alkaline earth catalyst, preferably calcium hydroxide, is utilized in the formation of the desired compounds. As the hydroxide is both a catalyst and a preferred method of keeping the pH within the desired range, it will be added as necessary to maintain the pH within the desired range. At the end of the reaction time, the alkaline earth salts may be removed by precipitation with a soluble carbonate salt such as sodium carbonate or sodium bicarbonate. This precipitate may then be filtered off leaving the sodium salt of the compound of the Summary in the aqueous solution. The pH of the reaction mixture is preferably greater than 10 and less than 14, with a desirable range being from about 10.5 to 12.5.

The temperature during the formation of the compounds of the present invention is conveniently maintained in the reactor at greater than 50° C., typically from 50° C. to 125° C., preferably 60° C. to 120° C.

The product as previously noted is conveniently isolated as the sodium salt. The reaction mixture may then be acidified to a pH of about 2 with an acid such as concentrated hydrochloric. The addition of the acid will result in the precipitation of fumaric acid which is then filtered from the reaction mixture. The filtrate may be evaporated to dryness in a rotary evaporator with the residue extracted with an excess of 2-butanol to separate the product from inorganic salts. This product is then filtered and the filtrate is evaporated to dryness. The product is then ready for use in its intended purpose. It should also be noted that the salts of the compounds of the present invention may also be used as a leached corrosion inhibitor such as by pumping the product into a well-hole and allowing it to slowly solubilize thereby protecting the piping in the well-hole from corrosion.

The products of the present invention are conveniently used as detergent builders in formulations with surfactants which include alkyl ether sulfates, alkyl benzene sulfonates, alkyl sulfates, olefin sulfonates, paraffin sulfonates, alkoxylated alcohols (especially ethoxylated alcohols) and alkyl polyglycosides and mixtures thereof. Conveniently, the novel detergent builders of the present invention are utilized in a weight ratio of from about 4:1 to about 1:4, preferably 3:1 to 1:3 by weight to the surfactant. The detergent products which may be formulated according to the present invention are conveniently used at from about 0.05 to 1% by weight of the wash liquor, e.g. water.

Detergent products formulated according to the present invention may also include a co-builder such as carboxymethyloxysuccinate (2-oxa-1,3,4-butanetricarboxylic acid); Builder M (2-oxa-1,1,3-propanetricarboxylic acid); zeolites including the type referred to in U.S. Pat. No. 4,019,999 issued Apr. 26, 1977 to Ohren et al. Similarly, citrates, carbonates and various phosphates including tripolyphosphate, pyrophosphates, and orthophosphates may be utilized as co-builders. The phosphate materials and a material such as the salts of nitrilotriacetic acid which may be used are, for the foregoing reasons, undesirable due to their environmental consequences. Nonetheless, should specific uses be desired, such materials may be utilized. Other convenient materials which may be utilized in formulating detergent products include sodium sulfate which is typically used as a structurant in a detergent product and sodium silicate which is useful as a structurant in granular detergent products and as well to protect washing machine surfaces from corrosion. Silicates also function to control pH in the wash liquor.

The following are suggested exemplifications of the present invention:

EXAMPLE I

Products of the present invention are prepared by reacting 19.7 parts of maleic anhydride in 100 parts water for about 15 minutes. 55.1 parts of glycerine are added followed by 27 parts of calcium hydroxide. The mixture is vigorously stirred and the temperature is raised to 100° C. The pH is maintained between 11 and 12.

After about one-half hour at 100° C., the mixture is cooled to 60°-75° C. by means of an air stream and five portions of 19 parts of maleic anhydride are added over time to the reaction mixture. A last portion of 58.8 parts of maleic anhydride is then added. The maleic anhydride is previously combined with 5 parts of water per part maleic anhydride prior to the addition to the reaction mixture. Each addition of maleic anhydride is followed by an equimolar addition of calcium hydroxide to maintain the pH at 11 to 12. The reaction is allowed to continue at 100° C. for an additional 3 to 3.5 hours.

The reaction is now essentially complete and the reaction mixture is allowed to cool to about 80°-90° C. At this time about 250 parts of sodium carbonate and sufficient water to keep the mixture fluid are added with vigorous stirring. The addition of sodium carbonate causes the calcium present in the reaction mixture to precipitate. The calcium carbonate is then filtered off after the reaction has been cooled to room temperature. The filtrate contains components as described in the Summary of the invention. The products of the present invention are determined to be more effective than sodium tripolyphosphate in their ability to sequester calcium ions from solution.

EXAMPLE II

A mixture of 0.45 parts of linear dodecyl benzene sulfonate and 0.25 parts of the builder listed below are added to 1000 parts of water containing calcium and magnesium for a total hardness level of 200 ppm as calcium carbonate in a 3:2 calcium to magnesium ratio. The mixture is adjusted to pH 9.0 and transferred to a tergotometer bucket which is preheated to 40.5° C. After agitation for 30 seconds, 6 soiled cloth (dacron/cotton blend) swatches with known reflectance values are added to each bucket. Agitation is continued at 125 rpm for 15 minutes. The cloth swatches are rinsed in water at 37° C. for 2 minutes and then dried in a clothes dryer for 15 minutes. The dried swatches are ironed before determination of the change in reflectance is made. The results are as follows:

| Builder | Reflectance Values |
| --- | --- |
| Sodium tripolyphosphate | 143 |
| Material of Example I | 173 |

A second test at a wash temperature of 49° C. gives similar results. At an equivalent weight level, the present builder outperforms sodium tripolyphosphate in calcium control. Products formulated as above give excellent hot or cold water cleaning ability.

EXAMPLE III

A product according to the present invention is prepared utilizing 20 parts builder prepared by Example I, 12 parts of the triethoxylated alcohol (dodecyl) and 50 parts water. The detergent product so formulated is fully miscible and shelf-stable, i.e. without separation of the components. The product, when tested, performs superior to a similarly formulated unbuilt detergent composition.

What is claimed is:

1. A compound of the formula:

MOOCCH$_2$(MOOC)HCOCH$_2$CH(OH)CH$_2$OCH-(COOM)CH$_2$COOM wherein M is a salt-forming cation or hydrogen or mixtures thereof.
2. The composition of claim 1 wherein M is hydrogen.
3. The composition of claim 1 wherein M is sodium.
4. The composition of claim 1 wherein M is potassium.
5. The composition of claim 1 wherein M is selected from the group consisting of ammonium and substituted ammonium compounds.
6. The composition of claim 1 wherein M is calcium.
7. The composition of claim 1 wherein M is magnesium.
8. The composition of claim 5 wherein M is ammonium.
9. The composition of claim 1 additionally comprising a surfactant material selected from the group consisting of alkyl ether sulfates, alkyl benzene sulfonates, alkyl sulfates, olefin sulfonates, paraffin sulfonates, alkyl polyglycosides, and alkoxylated alcohols, and mixtures thereof.
10. The composition of claim 9 wherein the surfactant is an alkyl polyglycoside.
11. The composition of claim 9 wherein the surfactant is an ethoxylated alcohol.
12. The composition of claim 1 containing a detergent builder selected from the group consisting of 2-oxa-1,3,4-butanetricarboxylic acid salts, 2-oxa-1,1,3-propanetricarboxylic acid salts, zeolites, citrate salts, carbonate salts, silicates, phosphate salts and salts of nitrilotriacetic acid.
13. The composition of claim 12 wherein the detergent builder is sodium carbonate.
14. The composition of claim 12 wherein the detergent builder is sodium tripolyphosphate.
15. The composition of claim 12 wherein the detergent builder is the sodium salt of nitrilotriacetic acid.
16. The composition of claim 1 prepared as a liquid detergent product.
17. A compound of the formula:

HOCH$_2$HC(OH)CH$_2$OCH(COOM)CH$_2$COOM wherein M is a salt-forming cation or hydrogen or mixtures thereof.
18. A compound of the formula:

HOCH$_2$CH[OCH(COOM)CH$_2$COOM]CH$_2$OCH-(COOM)CH$_2$COOM wherein M is a salt-forming cation or hydrogen or mixtures thereof.
19. A mixture of the compound of claim 17 and

MOOCCH$_2$(MOOC)HCOCH$_2$CH(OH)CH$_2$OCH-(COOM)CH$_2$COOM wherein M is a salt-forming cation or hydrogen or mixtures thereof.
20. A mixture of the compound of claim 18 and

MOOCCH$_2$(MOOC)HCOCH$_2$CH(OH)CH$_2$OCH-(COOM)CH$_2$COOM wherein M is a salt-forming cation or hydrogen or mixtures thereof.

* * * * *